United States Patent
Dunleavy et al.

(10) Patent No.: US 9,194,832 B2
(45) Date of Patent: Nov. 24, 2015

(54) STRUCTURAL HEALTH MONITORING USING SPRAYABLE PAINT FORMULATIONS

(75) Inventors: Michael Dunleavy, Bishopston (GB); Hazel Anne Dyke, Aust (GB); Sajad Haq, Glasgow (GB)

(73) Assignee: BAE SYSTEMS PLC, London (GB)

( * ) Notice: Subject to any disclaimer, the term of this patent is extended or adjusted under 35 U.S.C. 154(b) by 335 days.

(21) Appl. No.: 13/702,607

(22) PCT Filed: Sep. 13, 2011

(86) PCT No.: PCT/GB2011/051708
§ 371 (c)(1),
(2), (4) Date: Dec. 7, 2012

(87) PCT Pub. No.: WO2012/038720
PCT Pub. Date: Mar. 29, 2012

(65) Prior Publication Data
US 2013/0312535 A1    Nov. 28, 2013

(30) Foreign Application Priority Data

Sep. 20, 2010  (EP) ..................................... 10275098
Sep. 20, 2010  (GB) ..................................... 1015718.8

(51) Int. Cl.
*G01N 27/04*   (2006.01)
*B82Y 30/00*   (2011.01)
(Continued)

(52) U.S. Cl.
CPC .............. *G01N 27/041* (2013.01); *B82Y 30/00* (2013.01); *G01M 5/0033* (2013.01); *G01M 5/0041* (2013.01); *G01M 5/0083* (2013.01); *B01F 11/02* (2013.01); *B01F 2003/125* (2013.01); *G01N 33/32* (2013.01)

(58) Field of Classification Search
CPC ... B01F 11/02; B01F 2003/125; B82Y 30/00; G01M 5/0033; G01M 5/0041; G01M 5/0083; G01N 27/041; G01N 33/32

USPC .............. 526/319, 329.7, 348.8; 72/352, 363, 72/379.2, 379.6; 73/54.01, 54.43, 73/861.355, 864.22, 864.23, 866, 776
See application file for complete search history.

(56) References Cited

U.S. PATENT DOCUMENTS 5,897,696 A * 4/1999 Giordano et al. ................ 106/35
6,276,214 B1 * 8/2001 Kimura et al. ................... 73/795

(Continued)

FOREIGN PATENT DOCUMENTS

EP    1 845 124 A1    10/2007
EP    1 852 296 A1    11/2007

(Continued)

OTHER PUBLICATIONS

Notification Concerning Transmittal of International Preliminary Report on Patentability (Forms PCT/IB/326 and PCT/IB/373) and the Written Opinion of the International Searching Authority (Form PCT/ISA/237) dated Apr. 4, 2013, issued in corresponding International Application No. PCT/GB2011/051708. (7 pages).

(Continued)

*Primary Examiner* — Freddie Kirkland, III
*Assistant Examiner* — Fredrick Michael
(74) *Attorney, Agent, or Firm* — Maine Cernota & Rardin (57) ABSTRACT

The structural health of a structure such as an aircraft is monitored by spraying a paint formulation containing a loading of carbon nanoparticles to provide a paint layer forming part of a paint system. The paint layer forms a smart skin whose electrical properties may be monitored to determine structural health.

16 Claims, 5 Drawing Sheets

(51) Int. Cl.
*G01M 5/00* (2006.01)
*B01F 11/02* (2006.01)
*B01F 3/12* (2006.01)
*G01N 33/32* (2006.01)

(56) References Cited

U.S. PATENT DOCUMENTS

| | | | | |
|---|---|---|---|---|
| 7,194,912 | B2 * | 3/2007 | Jordan et al. | 73/774 |
| 7,730,547 | B2 * | 6/2010 | Barrera et al. | 850/21 |
| 7,786,736 | B2 * | 8/2010 | Thostenson et al. | 324/525 |
| 7,921,727 | B2 * | 4/2011 | Rice | 73/762 |
| 7,975,556 | B2 * | 7/2011 | Hatami et al. | 73/788 |
| 8,684,595 | B2 * | 4/2014 | Wardle et al. | 374/45 |
| 8,752,438 | B2 * | 6/2014 | Hatami et al. | 73/788 |
| 8,943,897 | B2 * | 2/2015 | Beauvais et al. | 73/777 |
| 2005/0284232 | A1 * | 12/2005 | Rice | 73/762 |
| 2007/0018142 | A1 | 1/2007 | Kwon et al. | |
| 2009/0121727 | A1 | 5/2009 | Lynch et al. | |
| 2011/0132245 | A1 * | 6/2011 | Shah et al. | 114/90 |
| 2014/0212656 | A1 * | 7/2014 | Rudhardt et al. | 428/323 |

FOREIGN PATENT DOCUMENTS

| | | |
|---|---|---|
| EP | 2 065 681 A1 | 6/2009 |
| WO | WO 2004/053464 A1 | 6/2004 |
| WO | WO 2004/065926 A1 | 8/2004 |
| WO | WO 2005/038824 A1 | 4/2005 |
| WO | WO 2006/004733 A1 | 1/2006 |

OTHER PUBLICATIONS

International Search Report (PCT/ISA/210) issued on Jan. 25, 2012, by the British Patent Office as the International Searching Authority for International Application No. PCT/GB2011/051708.

Written Opinion (PCT/ISA/237) issued on Jan. 25, 2012, by the British Patent Office as the International Searching Authority for International Application No. PCT/GB2011/051708.

Search Report issued on Dec. 10, 2010, by the British Patent Office for Application No. 1015718.8.

Search Report issued on Mar. 10, 2011, by the European Patent Office for Application No. 10275098.1.

Kang et al., "A carbon nanotube strain sensor for structural health monitoring", Smart Materials and Structures, Jun. 2006, pp. 737-748, vol. 15, No. 3.

Zhao et al., "Spray deposited fluoropolymer/multi-walled carbon nanotube composite films with high dielectric permittivity at low percolation threshold", Carbon, Science Direct, Mar. 2009, pp. 561-569, vol. 47, No. 3.

Kirikera et al., "A structural neural system for mechanical, biological, and environmental systems", Computers & Electrical Engineering, Science Direct, Feb. 2008, pp. 127-140, vol. 34, No. 2.

Kang et al., "Structural health monitoring based on electrical impedance of a carbon nanotube neuron", Key Engineering Materials Trans Tech Publications, 2006 (month unknown), pp. 140-145, vols. 321-323.

Zhao et al., "Spray deposition of polymer nanocomposite films for dielectric applications", Materials Science and Engineering, Jun. 2008, pp. 140-145, vol. 151, No. 2.

Aldraihem et al., "Nanocomposite functional paint sensor for vibration and noise monitoring", Sensors and Actuators, Feb. 2009, pp. 233-240, vol. 149, issue 2.

"Bridge Skin Could Reveal Cracks and Corrosion Beneath", ScienceDaily, Aug. 9, 2007, http://www.sciencedaily.com/releases/2007/08/070808094037.htm, retrieved Sep. 12, 2010.

Loh et al., "Carbon Nanotube Sensing Skins for Spatial Impact and Corrosion Detection", Journal of Nondestructive Evaluation, 2009 (month unknown), pp. 9-25.

Hou et al., "Spatial Conductivity Mapping of Carbon Nanotube Composite Thin Films by Electrical Impedance Tomography for Sensing Applications", Nanotechnology, 2007 (month unknown), pp. 1-9.

* cited by examiner

STRUCTURAL HEALTH MONITORING USING SPRAYABLE PAINT FORMULATIONS

This invention relates to a method of monitoring the structural health of a structure by spraying a paint formulation containing a dispersion of nanoparticles to form a component of a paint system applied to said structure. In this manner the structure is provided with a 'smart' skin whose electrical properties may be monitored to determine various selected structural health properties. The invention also extends to paint formulations for use in such a method and to structures treated in accordance with the method. The term structural health monitoring is used broadly to include simple strain sensing as well as other structural health detection such as damage detection, crack detection and crack propagation etc.

Structural health monitoring (SHM) has important implications in terms of support, maintenance and repair of military platforms and a low cost universal prognostics and diagnostics capability would significantly reduce the through-life costs. Unfortunately current SHM strategies suffer from complexity, high costs, limited spatial resolution and are dependent mainly on embedded sensors and are not always amenable to being retro-fitted or deployed over large areas without major disruption of the structure. There has been a proposal in WO2006/004733 to monitor the structural health of a composite structure by applying a conductive ink in a grid pattern and measuring changes in resistance across the grid to detect damage to the structure. In this arrangement the ink is not intrinsic to a conventional paint structure but is added as a pattern over or under a non-conductive insulating coating, or under a paint coat and the ink does not provide the robust environmental, abrasion-resistance properties provided by a paint. We have found that a grid structure is problematic on the external surfaces of an aircraft, particularly if the grid is left exposed because the airflow over the grid induces erosion at the interfaces between the grid and the underlying structure which can instigate damage. Furthermore, the provision of discrete grid lines rather than a continuous sensing surface, means that events in the interstices of the grid are not directly monitored. Also, the inks referred to in the earlier document are simple formulations comprising the nanofibres dispersed in solvent, with a thermoplastic polymer being added to form a homogenous dispersion, with no solids content other than the nanoparticles. A durable paint by contrast, and especially an aircraft paint, already has a high solids content with numerous fillers to control the material properties and to provide corrosion etc resistance, and so the amount of spare volume in the fluid paint for incorporation of the other material is low.

Although there is a mention that nanotubes may be used there is no indication of a sprayable paint formulation incorporating nanotubes.

In order to provide a suitable smart skin facility we have therefore designed a carbon nanoparticle-based paint system that is sprayable so that it can be applied over complex and large areas to detect, for example, strain.

Accordingly, in one aspect, this invention provides a method of monitoring the structural health of a structure which comprises applying by spraying a paint formulation containing a dispersion of carbon nanoparticles to provide a paint layer on said structure to form part of a durable paint system, and monitoring an electrical characteristic of said paint layer thereby to determine an indication of the structural health of said structure in the region of said paint layer.

Although there are numerous applications, a preferred application is that of providing a smart skin for an aircraft. In particular we have modified the formulation of standard aerospace qualified paint systems through the addition of carbon nanoparticles to render the material electrically conducting and to induce strain sensitivity. Aircraft paint systems are highly specialised, containing pigments, binders and fillers and the ability to incorporate strain sensitivity in such paint systems enables an arrangement to be provided in which the structural health monitor is effectively intrinsic to the original paint structure, and does not require modification or recertification of the structure. Furthermore, as there are tried and tested techniques for stripping paint off an aircraft and reapplying a paint system, the smart skin can be applied retrospectively.

The layer produced by spraying paint formulation may be the top coat of the paint system or it may be a primer or undercoat of the paint system. In either event it will be appreciated that a strain sensing function is achieved with minimal disruption of the paint formulation.

The paint formulation may be part of a polyurethane paint such as a two-part polyurethane paint system or it may be part of an epoxy system.

In order to assist dispersion of the carbon nanoparticles, the paint formulation may have a solvent added. In addition, or alternatively, the paint formulation may be subjected to a suitable energisation process such as sonication treatment to assist dispersion of the nanoparticles. Where sonication is applied, it is preferably effected over a plurality of spaced time intervals thereby to ensure that the temperature of the paint formulation does not exceed a predetermined value, for example to avoid excessive solvent loss. After sonication, the paint formulation is preferably allowed to cool prior to addition of a hardener before spraying.

Although other nanoparticles may be used, carbon nanotubes are preferred. The term 'nanotube' is used to mean a material with a cylindrical or toroidal structure of the fullerene family. Preferably said nanotubes have a mean length of between 0.05 nm and 20 nm and preferably with a mean diameter in the range of from 7 nm to 30 nm. In a particularly preferred formulation, the mean number of walls of the nanotubes is between 3 and 30. Preferably, the percentage loading of nanotubes in the formed paint layer is between 1% and 20% weight by weight. Preferably, the thickness of the sprayed paint layer lies within the range of from 10 μm to 300 μm. Advantageously, the resistivity gauge factor of the formed paint layer lies within the range of from 1 to 1000, although higher values are possible. The resistance gauge factor is preferably greater than 2000, more preferably above 600, and ideally above 800.

The paint layer may be monitored by detecting the respective electrical resistances between spaced parts of the continuous extended paint layer and thereby deducing at least one of the locations and magnitudes of a structural health parameter. The monitoring operation may be arranged to monitor for abrupt changes in resistance indicative of microstructure damage such as microcracking and to log these whilst continuing to monitor more gradual changes indicative of elastic and/or plastic deformation of the underlying structure.

In another aspect, this invention provides a structure including one or more paint layers including a dispersion of nanoparticles and a detector for detecting an electrical property of said paint layer, thereby to determine an indication of the structural health of said structure.

In another aspect, the invention extends to a paint formulation for use in a method as described above, comprising a dispersion of carbon nanotubes in a sprayable resin or polymeric material.

In yet another aspect, this invention provides a method for producing a paint formulation for use in a method as described above, which comprises providing a liquid component of an aerospace paint system, and dispersing in said liquid component an amount of carbon nanoparticles.

Whilst the invention has been described above, it extends to any inventive combination or sub-combination of the features set out below or in the accompanying claims.

The invention will be better understood by reference to the following examples, in which reference is made to the accompanying drawings in which.

We describe below preferred arrangements for providing a coating or smart skin made up of an aerospace qualified paint system that comprises a dispersion of carbon based nanotubes (CNT) within a paint matrix. A variety of dispersion methods, stabilisation strategies and concentrations of carbon nanotubes were evaluated to undertake the investigation of the SHM properties of the materials. The dispersion characteristics and the stability of the paint system were evaluated in tandem with the electrical behaviour of the paint. The dispersion characteristics of the nanotubes and the stability of the paint system affect both the electrical characteristics and the spraying characteristics.

EXAMPLES

Various formulations of paints were made up by taking commercially available aircraft paint systems and modifying them to incorporate various loadings of carbon nanotubes. Different nanotube concentrations and alternative thicknesses were investigated to assess the electrical properties of the painted structures. Various substrates were selected for painting and included glass, carbon fibre composites, glass fibre composites and aluminium (with a painted primer coating).

Example 1

Carbon nanotubes were dispersed in an aerospace qualified polyurethane top coat to provide a sprayable paint layer. The paint system in this example was made up a resin (Aviox 77702) a hardener (Aviox 90150) and an activator (Aviox 99321) all available from Akzo Nobel Advanced Coatings. Two formulations were prepared, one with 2% w/w carbon nanotubes and the other with 5% w/w. The relevant amount of carbon nanotubes (Graphistrength C100 carbon nanotubes available from Arkema, France) was added to the resin and activator having previously added butyl acetate as an extra solvent at 4.2 ml per gram of resin and activator. The nanotubes were dispersed using a high power ultrasonic probe (175 Wmin at 25 kHz frequency) at a duty cycle of 15 minutes on and 15 minutes off for two cycles. The duty cycle is used to ensure that not too much solvent evaporates, with the maximum temperature being kept below 100° C., by active cooling using cold water or an ice/water cooling bath. Once the carbon nanotubes have been fully dispersed, the resin was stored. The resultant dispersion of nanotubes in resin was found to be stable for at least 24 hours.

Figure 1:
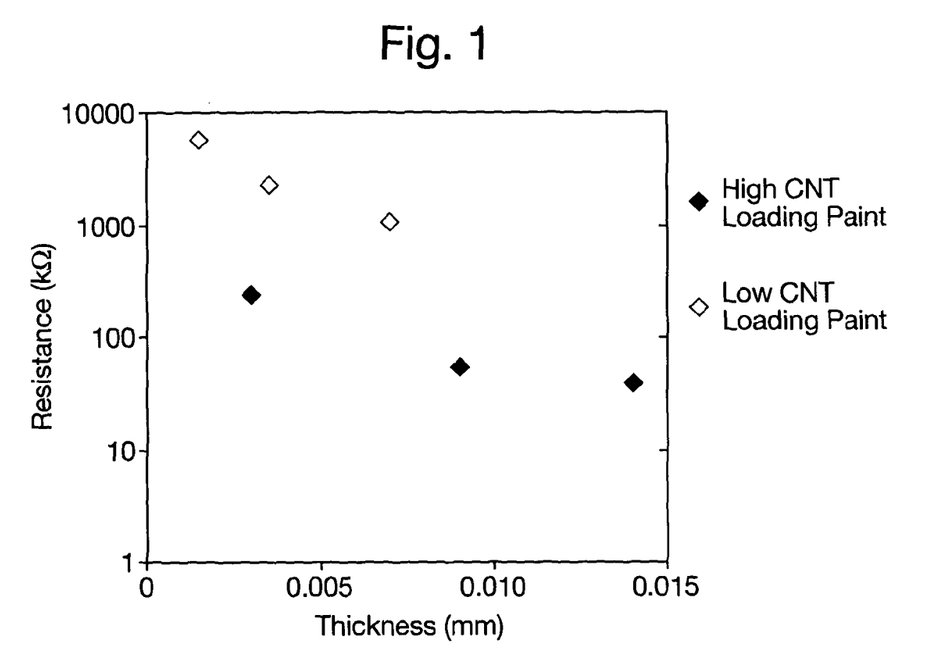
FIG. 1 is a graph showing the resistance of a paint sensor on a glass fibre composite as a function of paint thickness and loading of carbon nanotube.

In order to use the paint system, the hardener is added to the resin once cool and immediately before spraying. The spray gun is tuned to find a setting that gives a smooth consolidated coat. The settings for the spray gun will depend on the particular application and the airflow and other conditions in the spray booth which should be controlled to give the required finish. The selection of appropriate settings and spray booth conditions is within the competence of one skilled in the art. The resistance of the films produced by spraying the paint formulation were measured and the results are shown in FIG. 1. The notable feature of these results is the fact that it is possible to tailor the conductivity of the material over greater than 2 orders of magnitude by altering the material thickness and nanotube concentration.

Figure 2:
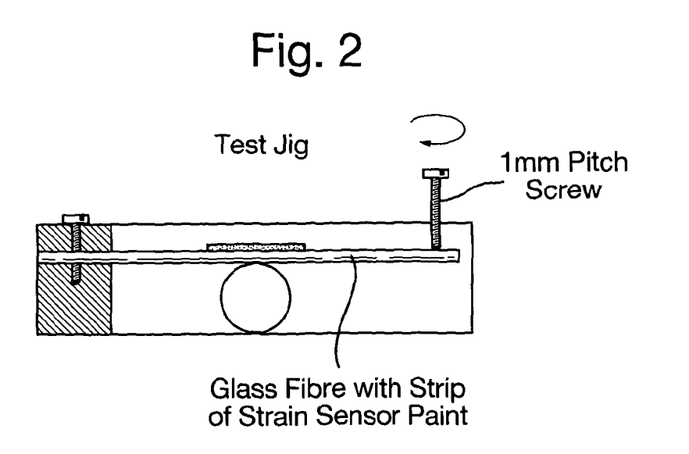
FIG. 2 is a schematic view of a test jig used in studies for strain measurement.

In order to screen the large number of samples generated for their strain behaviour (measured by a change in resistance) a simple 3 point bend experimental set up was established to allow deflection of the substrates in a cantilever formation. The test jig is shown in FIG. 2 and was calibrated using a commercial strain sensor attached to a glass fibre substrate. Results on the nanotube sensors were collected both in tension and compression by reversing the sample orientation in the jig. The resistance data was collected by deflecting the composite from its stress free position to its maximum deflection and then back to its original starting position.

Figure 3:
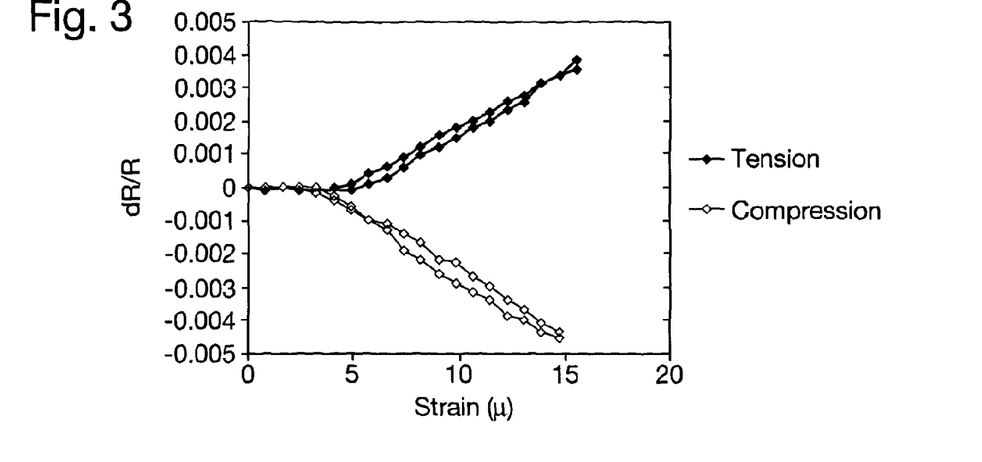
FIG. 3 is a graph showing normalised resistance (dR/R) versus strain in compression and tension for increasing and decreasing loads.

A representative data set is shown plotted in FIG. 3 for the tension and compression measurements with both increasing and decreasing loads plotted for each case. This graph shows that the resistance change increases linearly with strain in both compression and tension. It is notable that the gradient of the curve, (the sensor sensitivity or the "gauge factor"), is different in compression and in tension. FIG. 3 also shows that as the load is decreased after the maximum strain has been applied, the resistance returns to the value obtained during the increasing load cycle, i.e. the increasing and decreasing load cycle curves are superimposed on each other.

Figure 4A:
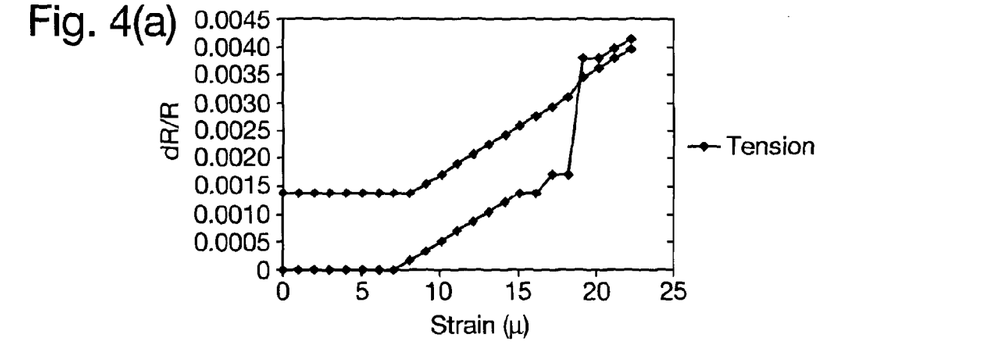
FIGS. 4(a) and (b) are graphs showing normalised resistance versus strain in compression and tension respectively for increasing and decreasing loads showing a discontinuity in resistance.
Figure 4B:
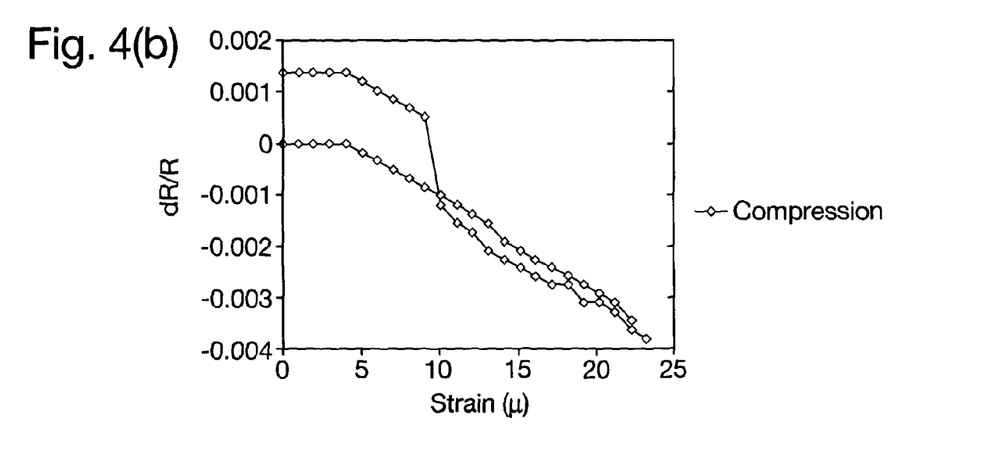

In some cases however systematic shifts in the normalised resistance data were observed during the strain cycles as shown in FIGS. 4(a) and (b). This shows that a sharp increase (decrease) in the resistance occurs at a certain deflection during the tension (compression) strain cycle. Note that after this discontinuity the new resistance is maintained during the load removal and that the resistance-strain gradient remains at its original value, i.e. the sensitivity of the sensor remains unchanged. It is thought that the change in resistance may be as a result of small scale damage to the paint film and in some of our samples we have observed the appearance of microcracks in the paint film.

This is an important advantage because it allows the paint layer to continue to monitor strain even after an irreversible microcracking event. The microcracking event may be in the paint itself which may provide an advance warning of the risk of damage to the underlying structure.

Figure 5:
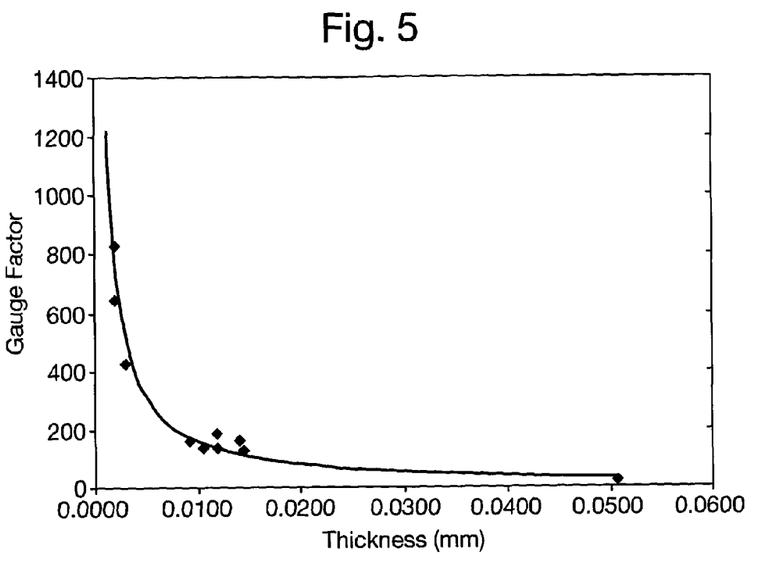
FIG. 5 is a graph showing gauge factor versus paint thickness for one particular nanotube concentration.
Figure 6:
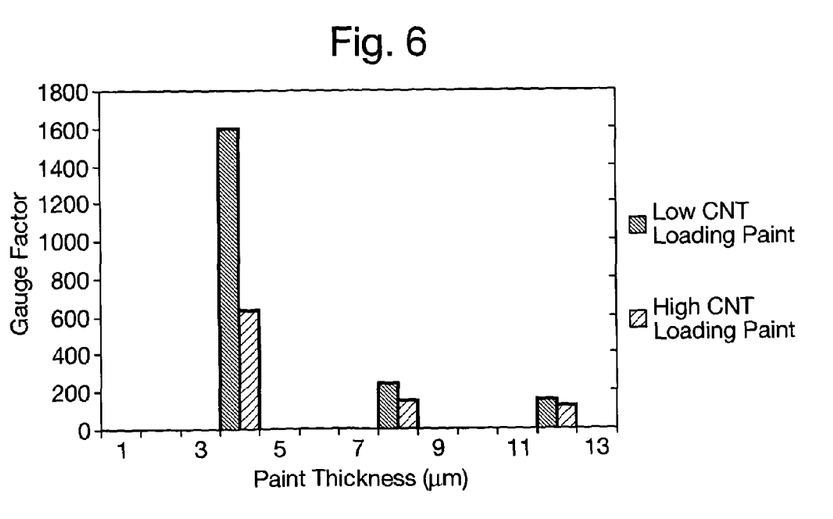
FIG. 6 is a graph showing a comparison of gauge factor for low and high concentration samples for various paint thicknesses.

The sensitivity of the paint film is dependent upon the thickness of the paint and the nanotube concentration. Highly sensitive sensors can be designed by optimising either of these parameters and the relationship with thickness is shown in FIG. 5 and with concentration in FIG. 6. FIG. 5 shows that for a given nanotube concentration the sensitivity drops dramatically as the paint thickness increases. FIG. 6 shows a comparison of two different concentrations and illustrates that for any given thickness the lower concentration material has the highest gauge factor or sensitivity.

The effect of using the active nanotube paint materials as an embedded sensor was also investigated by overcoating the CNT paint with a qualified aerospace topcoat paint material. The analysis showed no difference in the resistance/strain data from the uncoated material with data similar to that of FIG. 3 obtained. Other conclusions from these studies are that the change in resistance is directly proportional to the applied strain in both compression and tension; the sensitivity or gauge factor (given by the gradient of the normalised resistance-strain curve) is different in compression and tension; high gauge factors can be achieved; the gauge factor decreases with paint thickness; the gauge factor decreases with increasing nanotube concentration, and overcoating the sensor with a passive paint system has no discernible effect on the strain behaviour.

Aluminium substrates were also sprayed with CNT loaded paint to investigate the strain sensing response on a material with different mechanical properties than the glass fibre composites and allowed the application of greater strains than with the glass fibre composite materials (up to 6% c.f. 0.01%). Two sizes of sensor patches were evaluated for resistive strain gauge characteristics. A larger patch had the dimensions 20 mm by 20 mm, and a smaller patch had dimensions of 20 mm by 1.5 mm. These samples were tested with a static load using an Instron testing machine under a tensile configuration rather than through the application of bending moments as employed for the glass fibre composites.

Figure 7:
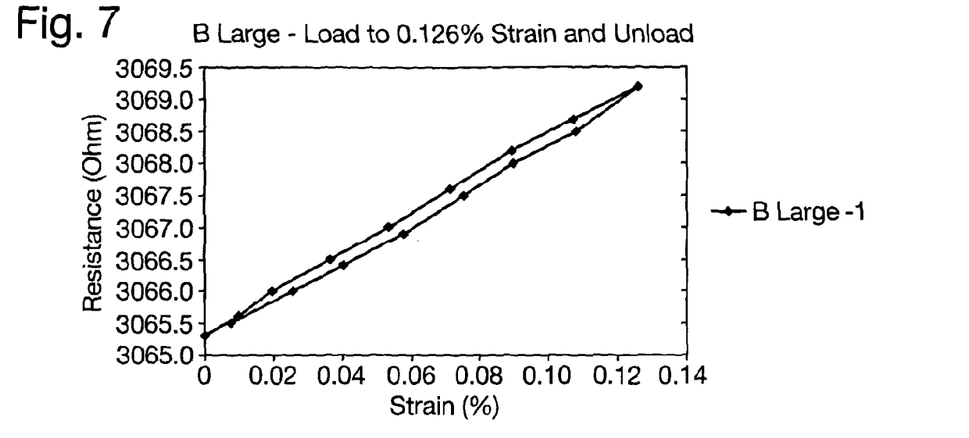
FIG. 7 is a graph showing the resistance of a sample in a low strain regime.

Strain values of up to 0.06 were applied to investigate the onset of a non-linear gauge factor of the sensors as the substrate approaches its elastic limit which occurs at around 0.4% strain. The response of the paint is not dissimilar to the material on the glass fibre composite. FIG. 7 plots the resistance of the large patch of one of the samples in the low strain regime. The upper line corresponds to the increasing load and the lower line to decreasing load. This shows that in this strain regime there is good linear response and the gauge factor is ~1.0. Note that the thickness of the films and the nanotube paint concentrations are such that a low gauge factor (as per FIGS. 5 and 6) is expected. There is some hysteresis but upon removing the load (zero strain) the resistance returns to its starting value.

Figure 8A:
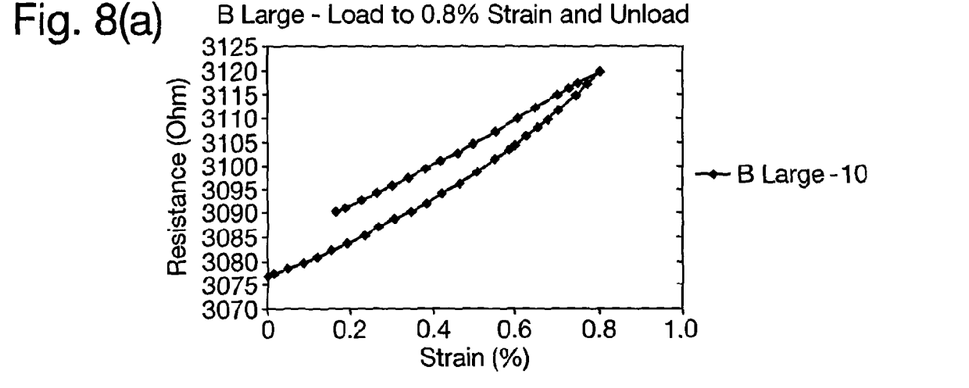
FIGS. 8(a) to (c) are graphs of resistance versus strain for loading and unloading cycles at 0.8, 1 and 3% strain values respectively.
Figure 8B:
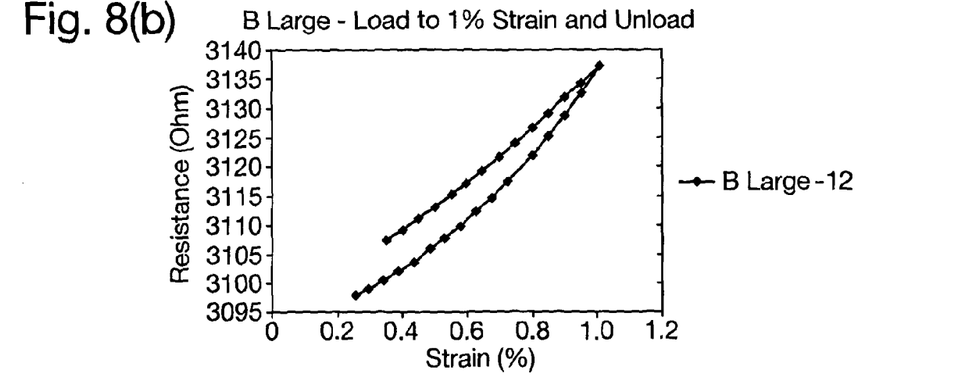
Figure 8C:
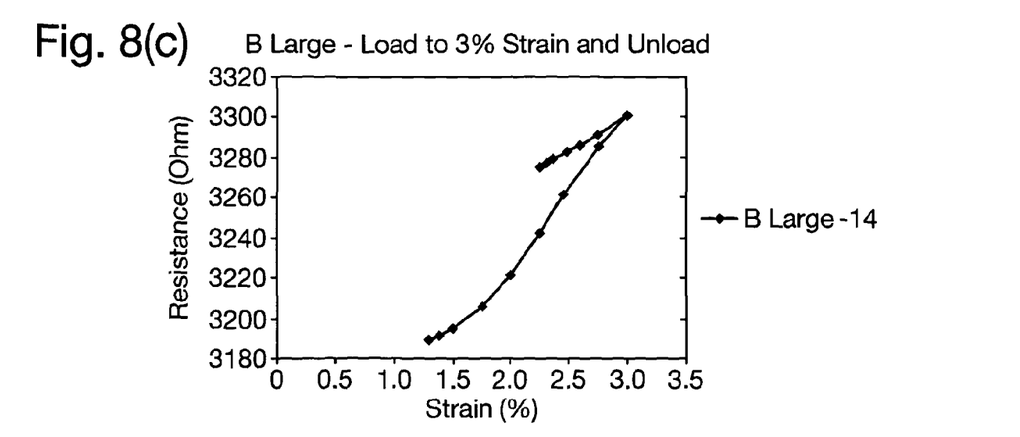
Figure 9:
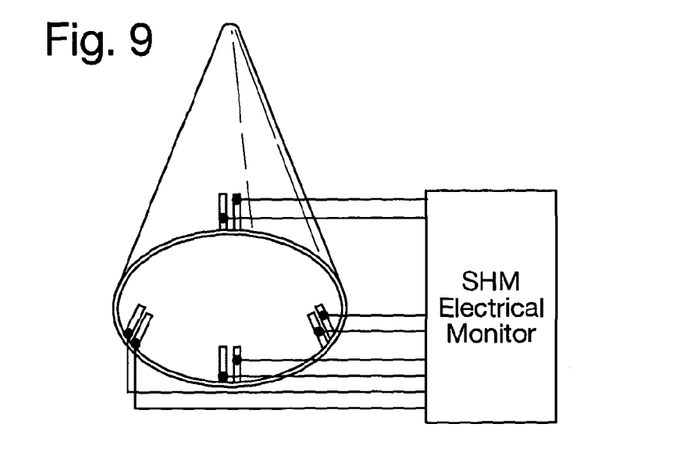
FIG. 9 is a schematic view of an electrode configuration for a paint sensor provide on a radome.
Figure 10:
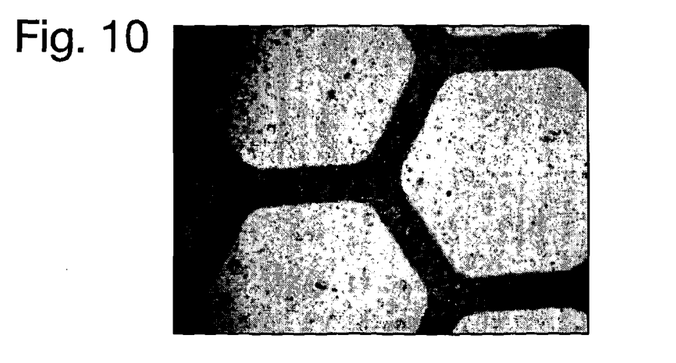
FIG. 10 is a view on an enlarged scale of a laser machine pattern produced on a nanotube paint coating.

Similar results were obtained with higher strains but upon unloading the sample an offset in the resistance was observed. As the strain is increased further the difference between the loaded and unloaded resistance values also increases. FIGS. 8(a), (b) and (c) show the successive increase in this offset as samples were measured at strains greater than the 0.4% elastic limit of the aluminium.

In order to demonstrate the ability to apply the sensing paint to a large area and complex shaped structure, a fibre composite radome was coated with the nanotube paint over a series of electrodes applied underneath the painted surface. The pairs of electrodes were applied at the bottom edge of structure with spacings of 1 cm and were distributed as shown in FIG. 8.

Electrical connections were made between different pairs of electrodes and also between alternate electrodes. Upon flexing the radome it was possible to discriminate between tensile and compressive strains by monitoring the change in resistance between the various electrodes. The absolute value of the resistance could be altered depending on the electrode configuration and which of the above electrodes are monitored. The extent and location of strains and other events may be determined by triangulation of the values from respective electrode pairs. In one arrangement the system may be calibrated and a look-up table constructed to relate the resistance values detected to the location and extent of the event.

The above Examples and investigations show that nanotube based paint systems may be designed to provide high sensitivity to strain and tailored to allow strain measurements over large values. It is possible to discriminate between tensile and compressive strains and this can be undertaken on a range of material systems, including fibre composites and metallic structures. The nanotube paint system is extremely robust and remains active even when strained many times past the elastic limit of aluminium. The active paint system also allows the detection of micro-damage to paint systems thus potentially providing a prognostic and diagnostic capability for military platforms. The nanotube paint may be used as an embedded system or as an overcoat within an otherwise conventional paint scheme. The active paint is sprayable and compatible with current commercial spraying methodologies and allows the detection of strain without embedding or use of sensors with can be mechanically disruptive to composite structures. Spraying of the material allows the application onto large area and complex structures as well as detailed and realistic (i.e. non-smooth) surfaces.

These studies indicate that it is possible to utilise nanotube modified commercial paint systems for structural health monitoring by measuring the change in strain induced resistance of the paint. The high sensitivities and wide range of strains make the material system amenable to a whole host of platform types for land, sea and air applications. The sensor paint is extremely robust and may be applied over large areas and complex shaped components using standard production spray facilities. The lightweight nature of the coating ensures that the solution is of low mass and indeed does not significantly increase the overall weight of a coated platform over and above conventional painted vehicles. The mass savings over conventional strain sensors coupled with the large area and high resolution mapping capability indicate significant potential for structural health monitoring without the cost and performance limitations of current systems.

Strain sensing in both tensile and compression configurations show that highly sensitive strain sensors can be fabricated and that they show a linear normalised resistance relationship with strain. By tailoring the paint thickness and the dispersion of the nanotubes it is possible to achieve gauge factors many times that of commercially available sensors indicating high sensitivity of the nanotube paint for strain detection. Suitable choice of paint formulation allows the detection of a wide range of strains that are applicable to military platforms and environments. Furthermore, it is possible to discriminate between tensile and compressive stresses through the strain response characteristics. In addition damage to the films at high strains may also be detected through discontinuities in the strain characteristics. The nanotube paint system also demonstrates its robustness by maintaining its linear response and sensitivity (gauge factor) post-damage illustrating that its operation is not compromised. The nanotube paint material may be deployed as a topcoat or also embedded as an active layer within a paint scheme (e.g.

as a primer) and the latter was demonstrated to have no discernible effect on the sensor sensitivity and linearity.

The invention claimed is:

1. A method of monitoring structural health of a structure, the method comprising:
    applying a sonification treatment to a paint formulation containing a dispersion of carbon nanoparticles to assist dispersion of said carbon nanoparticles;
    spraying said paint formulation containing said dispersion of carbon nanoparticles to provide a paint layer on said structure to form part of a durable paint system; and
    monitoring an electrical characteristic of said paint layer to thereby determine an indication of the structural health of said structure in a region of said paint layer.

2. A method according to claim 1, wherein the layer comprises:
    a top coat of the paint system.

3. A method according to claim 1, wherein the layer comprises:
    a primer layer of the paint system.

4. A method according to claim 1, wherein said paint formulation comprises:
    a two or more part polyurethane paint.

5. A method according to claim 1, wherein said paint formulation comprises:
    an epoxy system.

6. A method according to claim 1, comprising:
    adding a solvent to the paint formulation to assist dispersion of said carbon nanoparticles.

7. A method according to claim 1, wherein said sonification treatment is effected over a plurality of spaced time intervals.

8. A method according to claim 1, comprising:
    after said sonification treatment, allowing the formulation to cool prior to addition of a hardener before spraying.

9. A method according to claim 1, wherein said carbon nanoparticles comprise:
    carbon nanotubes.

10. A method according to claim 9, wherein said carbon nanotubes have a mean length of between 0.05 nm and 20 nm.

11. A method according to claim 9, wherein a mean diameter of the carbon nanotubes lies in a range of 7 nm to 30 nm.

12. A method according to claim 9, wherein the carbon nanotubes have a mean number of walls of between 3 and 30.

13. A method according to claim 9, wherein a percentage loading of carbon nanotubes in the paint layer is between 1% and 20% by weight.

14. A method according to claim 1, wherein a thickness of the paint layer lies within a range of 10 μm to 300 μm.

15. A method according to claim 1, wherein a resistivity gauge factor of the paint layer lies within a range of 1 to 1000.

16. A method according to claim 1, comprising:
    applying said paint layer as a continuous layer over an extended region to be monitored.

* * * * *